United States Patent [19]

Jackson et al.

[11] Patent Number: 5,087,756
[45] Date of Patent: Feb. 11, 1992

[54] 3-HYDROXY-2-CYCLOBUTEN-1-ONE SALTS

[75] Inventors: Barry Jackson, Glis; Thomas Scholl, Visp, both of Switzerland

[73] Assignee: Lonza Ltd., Gampel/Valais, Switzerland

[21] Appl. No.: 658,707

[22] Filed: Feb. 21, 1991

[30] Foreign Application Priority Data

Feb. 26, 1990 [CH] Switzerland ............... 598/90

[51] Int. Cl.$^5$ ............................... 35C 211/63
[52] U.S. Cl. ................... 564/457; 564/462; 564/463; 564/1; 568/381
[58] Field of Search ............ 564/281, 457, 462, 463; 568/381, 851

[56] References Cited

U.S. PATENT DOCUMENTS

| | | | |
|---|---|---|---|
| 4,104,308 | 8/1978 | Gadek et al. | 568/381 |
| 4,461,681 | 7/1984 | Barber | 204/59 R |
| 4,523,980 | 6/1985 | Barber | 204/59 R |

FOREIGN PATENT DOCUMENTS

| | | |
|---|---|---|
| 2235882 | 2/1973 | Fed. Rep. of Germany . |
| 2618557 | 11/1977 | Fed. Rep. of Germany . |
| 2623836 | 12/1977 | Fed. Rep. of Germany . |
| 2824558 | 12/1979 | Fed. Rep. of Germany . |
| 3314431 | 10/1984 | Fed. Rep. of Germany . |

OTHER PUBLICATIONS

Agnew. Chem., 20, (1966), p. 931.
Roedig. A., and Bernemann, P., Liebigs Ann. Chem. (1956), 600, pp. 1 to 11.
Maahs, G., Liebigs Ann. Chem., (1965), 686, pp. 55–63.
Agnew, Chemie, (1963) 75, p. 982.
Fan. R., et al., Chemical Abstracts, (1987), 106 103798c.
Maahs, G., and Hegenberg, P., Angew. Chemie, (1966) 78, pp. 927 to 931.
Schmidt, A. H., and Ried, W., Synthesis, (1978) pp. 869 to 880.
Paine, A. J., Tetrahedron Letters, (1984), 25, pp. 135 to 138.
Silvestri, G., et al., Gass. Chim. Itl., (1972), 102, pp. 818 to 821.

Primary Examiner—Robert W. Ramsuer
Assistant Examiner—Jessica H. Nguyen
Attorney, Agent, or Firm—Fisher, Christen & Sabol

[57] ABSTRACT

3-Hydroxy-2-cyclobuten-1-one salts of the general formula:

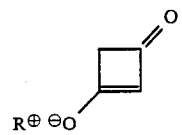

wherein R is an ammonium group of the general formula:

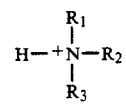

wherein $R_1$, $R_2$ and $R_3$ are the same or different in meaning and each is a hydrogen atom, a lower alkyl group or a cycloalkyl group or R is an alkali metal atom. The salts according for formula I are obtained by the reaction of pure 3-acetoxy-2-cyclobuten-1-one, or 1,3-cyclobutanedione or a distillation residue of the diketene production containing 3-acetoxy-2-cyclobuten-1-one, with a base. The base can be an amine of the general formula:

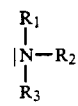

wherein $R_1$, $R_2$, and $R_3$ have the above-mentioned meaning, or an alkali metal alcoholate or an alkali metal hydroxide. The salts according to formula I are suitable for the production of squaric acid, by their being halogenated in a first step and then being hydrolyzed to squaric acid in a second step.

10 Claims, No Drawings

3-HYDROXY-2-CYCLOBUTEN-1-ONE SALTS

BACKGROUND OF THE INVENTION

1. Field Of The Invention

The invention relates to new 3-hydroxy-2-cyclobuten-1-one salts as well as processes for their production and their use, especially for the production of squaric acid.

2. Background Art

Squaric acid is an interesting intermediate product for the production of pharmaceutical agents, dyes [Angew. Chem. 20, (1966), p. 931]and herbicides (Swiss Patent No. 609,837). Various processes for the production of squaric acid are known from the literature.

Several processes start from hexachloro-1,3-butadiene, which is cyclized to a chlorinated cyclobutene derivative with the help of sodium ethanolate. These intermediate products are hydrolyzed to squaric acid with sulfuric acid or other acids [Roedig, A., and Bernemann, P., Liebigs Ann. Chem., (1956), 600, p. 1; Maahs, G., Liebigs Ann. Chem., (1965), 686, p. 55; Angew. Chemie, (1963), 75, p. 982; Uehara, A., and Tsuchiya, R., Sci. Rep. Kanazawa Univ., (1980), 25, p. 83; Fan, R., et al., Chemical Abstracts, (1987), 106, 103798c]. Instead of sodium ethanolate, morpholine is also used [Maahs, G., and Hegenbero, P., Angew. Chemie, (1966), 78, p. 927; Schmidt, A. H. and Ried, W., Synthesis, (1978), p. 869; Gadek, T. R., et al., (1976), U.S. Pat. No. 4,104,308; Paine, A. J., Tetrahedron Letters, (1984), 25, p. 135]. The cyclization can also take place purely thermally [Mueller, W., (1976), German PS 2,618,557; Schroeder, M., and Schaeoer, W. (1976), DE-PS 2,623,836; Maahs, G., and Rombusch, D., (1978), German PS 2,824,558; Rombusch. K., and Maahs, G.. (1983), German OS 3,314,431]. Drawbacks of all of these processes are either modest yields or high expenses (e.g., distillation with an extreme reflux ratio) and the special safety measures, which are necessary during handling of the carcinogenic feedstock hexachloro-1,3-butadiene.

According to another process [Bellus, D., et al., Helv. Chim. Acta, 61, (1978), p. 1784], squaric acid in a 70 percent yield is obtained from the fungus metabolite moniliformin by bromination and hydrolysis. But moniliformin occurs in nature only in small amounts, and the known synthesis for it are expensive and produce only modest yields.

A further process, that is, the electrochemically reductive tetramerization of carbon monoxide to squaric acid, requires considerable equipment and yields a product mixture from which squaric acid is difficult to obtain in pure form. [Silvestri, G., et al. Gazz. Chim. It., (1972), 102, p. 818; German OS 2,235,882; U.S. Pat. No. 4,461,681; U.S. Pat. No. 4,523,980; Fabre, P. L., et al., Bull. Soc. Chim. Fr., (1988), p. 933].

BROAD DESCRIPTION OF THE INVENTION

The main object of the invention is to provide a new synthesis of squaric acid, which, starting from easily accessible feedstocks, produces squaric acid at modest expense in a good yield and purity. The main object of the invention is achieved by having found new intermediate products, which can be produced from an easily accessible feedstock and from which squaric acid can be produced without great expense.

Other objects and advantages of the invention are set out herein or are obvious herefrom to one skilled in the art.

The objects and advantages of the invention are achieved by the compounds and processes of the invention.

The intermediate products according to the invention have the formula:

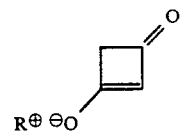

I wherein R is an ammonium group of the formula;

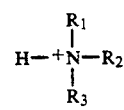

II wherein $R_1$, $R_2$ and $R_3$ are the same or different in means and each is a hydrogen atom, a lower alkyl group or a cycloalkyl group, or R is an alkali metal atom. Preferred radicals $R_1$, $R_2$ and $R_3$ of the ammonium group are a hydrogen atom, a $C_1$–$C_4$ lower alkyl group or a cyclohexyl group, especially a hydrogen atom, a methyl group, an ethyl group or a cyclohexyl group. If R is an alkali metal atom, the alkali metals sodium and potassium are preferred.

The preferred compounds of general formula I are:
3-hydroxy-2-cyclobuten-1-one diethylammonium salt
3-hydroxy-2-cyclobuten-1-one cyclohexylammonium salt·
3-hydroxy-2-cyclobuten-1-one cyclohexyldimethylammonium salt
3-hydroxy-2-cyclobuten-1-one dicyclohexylammonium salt
3-hydroxy-2-cyclobuten-1-one dicyclohexylmethylammonium salt
3-hydroxy-2-cyclobuten-1-one ammonium salt
3-hydroxy-2-cyclobuten-1-one sodium salt
3-hydroxy-2-cyclobuten-1-one potassium salt The initial material used for the process of the invention is 3-acetoxy-2-cyclobuten-1-one, which is designated below as triketene, optionally a distillation residue of diketene production with a triketene content of suitably 5 to 60 percent by weight, or 1,3-cyclobutanedione.

The above-mentioned initial materials are converted with a base to an end product according to formula I. As the base, an amine of the formula:

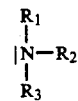

III wherein $R_1$, $R_2$ and $R_3$ have the above-mentioned meaning, or an alkali metal alcoholate or an alkali metal hydroxide is suitably used. Preferably cyclohexyldimethylamine, dicyclohexylamine, diethylamine, cyclohexyldimethylamine, dicyclohexylmethylamine or ammonia can be used as amines of formula III.

The reaction of triketene as the initial material is suitably performed with 0.5 to 4 moles of an amine of formula III, relative to 1 mol of triketene. The reaction of 1,3-cyclobutanedione as the initial material is suitably performed with 0.5 to 4 mols of an amine of formula III, preferably with 0.5 to 1.5 mol, relative to 1 mol of 1,3-cyclobutanedione.

The reaction is usually performed at a temperature of −40° to 50° C., preferably 10° to 25° C. After a reaction time of 15 minutes to 5 hours, the end product according to formula I can be obtained by the usual working up, e.g., by (filtration.

As a solvent, low-boiling, aliphatic alcohols, $C_1$-$C_4$ carboxylic acids, $C_1$-$C_4$ carboxylic acid esters, low-boiling ethers and ketones, nitriles and aromatic hydrocarbons can be used. Representatives of these solvent groups are, for example, acetone, toluene, diethyl ether, diisopropyl ether, t-butyl methyl ether and dichloromethane, ethanol, acetonitrile, acetic acid and ethyl acetate; preferably ethyl acetate, ethanol or acetonitrile is used.

The 3-hydroxy-2-cyclobuten-1-one salts according to formula I can also be produced by reaction of the initial materials with 0.8 to 2.5 moles of an alkali metal alcoholate or an alkali metal hydroxide, such as, with sodium hydroxide, potassium hydroxide, sodium ethanolate, potassium ethanolate, sodium methanolate or potassium methanolate, relative to 1 mol of initial material, and preferably with 0.8 to 1.2 mol of sodium hydroxide, potassium hydroxide, sodium methanolate or sodium ethanolate.

The reaction, as with the reaction of the initial material with the amine according to formula III, is suitably performed at a temperature of −40° to 50° C., preferably 10° to 25° C. After a reaction time of 15 minutes to 5 hours, the end product according to formula I can be obtained by the usual working up, e.g., filtration. As the solvents, the same solvents as those described previously can be used.

The new 3-hydroxy-2-cyclobuten-1-one salts can also be produced in two steps, by triketene being converted in a first step by acidic hydrolysis to 1,3-cyclobutanedione and this intermediate product then being converted in a second step to the 3-hydroxy-2-cyclobuten-1-one salt, as already described. As the acid, sulfuric acid, hydrochloric acid, formic acid and trifluoroacetic acid can be used, preferably aqueous formic acid in excess is used. The hydrolysis is usually performed at a temperature of 0° to 30° C., preferably of 15 to 30. After a reaction time of 15 minutes to 24 hours, as a rule, the 1,3-cyclobutanedione can be worked up in the usual way, suitably extraction and recrystallization The new 3-hydroxy-2-cyclobuten-1-one salts according to formula I are suitable for the production of squaric acid, and squaric acid is isolated in a good yield and purity, or they can again be used for production of 1,3-cyclobutanedione.

For production of squaric acid, the 3-hydroxy-2-cyclobuten-1-one salts according to formula I are halogenated in a first step and then hydrolyzed to squaric acid in a second step.

In the first step, the halogenation of the 3-hydroxy-2-cyclobuten-1-one salt is suitably performed with 2 to 4 of bromine, chlorine or sulfuryl chloride relative to 1 mol of the initial material, preferably with 2.5 to 3.5 moles of bromine. The halogenation can also be performed first with 0.25 to 1 mol of bromine and then with 2.0 to 3.0 moles of chlorine or sulfuryl chloride, relative to 1 mol of the initial material. The halogenation is usually performed at a temperature of −40° to +40° C., preferably of −25° to 25° C. After a reaction time of suitably 30 minutes to 4 hours, the halogenated cyclobutenone can be isolated in a good yield or directly hydrolyzed further to squaric acid. $C_1$-$C_4$ carboxylic acids, $C_1$-$C_4$ carboxylic acid ethyl esters, carboxylic acid anhydrides and chlorinated hydrocarbons can be used as the solvents. Representatives of these solvent groups are, for example, acetic acid, ethyl acetate, acetic anhydride, carbon tetrachloride, methylene chloride and chloroform; preferably acetic acid, ethyl acetate or methylene chloride is used.

In the second step, the hydrolysis to squaric acid can be performed with mineral acids, such as, sulfuric acid, hydrochloric acid, hydrobromic acid, phosphoric acid, with sulfonic acids, such as, aqueous methanesulfonic acid, with water or with carboxylic acids, such as, aqueous formic acid and aqueous trifluoroacetic acid. Preferably mineral acids, such as, concentrated sulfuric acid or hydrochloric acid, carboxylic acids, such as, aqueous formic acid, or sulfonic acids, such as, aqueous methanesulfonic acid, are used in excess. The hydrolysis is suitably performed at a temperature of 50° to 150° C., preferably at a temperature of 90° to 100° C. The hydrolysis to squaric acid with water is performed by reflux. After a reaction time of 2 to 48 hours, squaric acid is obtained in a good yield.

The new 3-hydroxy-2-cyclobuten-1-one salts according to formula I are valuable, stable substances. On the one hand, they are equivalents for the 1,3-cyclobutanedione decomposing at room temperature or synthetically interesting, and, on the other hand, they are the intermediate products of a new synthesis of squaric acid.

DETAILED DESCRIPTION OF THE INVENTION

EXAMPLE 1

Production of 1,3-cyclobutanedione starting from triketene 4.1 g of triketene (33 mmol) was dissolved in 10 q of sulfuric acid and 30 g of ice. After 15 minutes, the mixture was extracted with methylene chloride (2 times 25 ml each), then dried on calcium chloride, filtered and concentrated by evaporation. 2.1 g of the solid material which was concentrated by evaporation was suspended in diethyl ether (10 ml), then the mixture was filtered and recrystallized in acetonitrile (13 ml). After the recrystallization, 1.57 g of 1,3-cyclobutanedione (18.7 mmol), corresponding to a yield of 57 percent, relative to the triketene used, was obtained.

EXAMPLE 2

Production of 3-hydroxy-2-cyclobuten-1-one-diethylammonium salt (a) 2.1 g of 1,3-cyclobutanedione (23.0 mmol) was suspended in 40 g of ethyl acetate. A solution of 1.84 g of diethylamine (25.0 mmol) in 10 g of ethyl acetate was instilled in this suspension at 20° C. within 15 minutes. After 1 hour of stirring at room temperature, the suspension was filtered and then dried. 3.05 g of the title product with a purity (according to HPLC) of 93.7 percent, corresponding to a yield of 79.2 percent, relative to the cyclobutanedione, was obtained. Data for the title compound was:

Melting point: 93° C. -94° C.

(b) A solution of 3.67 g of diethylamine (99.5 percent; 0.0 mmol) in 10 g of ethyl acetate was instilled in a solution of 3.25 g of 3-acetoxy-2-cyclobuten-1-one (triketene, content, 97 percent; 25.0 mmol) in 40 g of ethyl acetate at 0° C. within 18 minutes. The reaction mixture was stirred for another hour at room temperature, then filtered and dried under vacuum. 3.75 g of the title product with a purity of 4.1 percent (according to HPLC), corresponding to a yield of 9.8 percent, relative to the 3-acetoxy-2-cyclobuten-1-one, was obtained. Data for the title compound was:

Melting point 94° C.-96° C.

$^1$H-NMR: (CDCl$_3$, 300 MHz) δin ppm 1.38 t, J=9 Hz, 3H.

30.1 q, J=9 Hz, 2H.

2.90 s, 2H.

4.35 s, 1H.

9.5 b, 2H.

EXAMPLE 3

Production of 3-hydroxy-2-cyclobuten-1-one-cyclohexyldimethylammonium salt (a) A solution of 3.21 g of N,N-dimethylcyclohexylamine (99 percent; 25.0 mmol) in 10 g of ethyl acetate was instilled in a suspension of 2.1 g of 1,3-cyclobutanedione (91.9 percent; 23.0 mmol) in 40 g of ethyl acetate at 20° C. in 15 minutes. After 1 hour of stirring at room temperature, the suspension was filtered and dried under vacuum. 4.27 g of the title product with a purity of 94.8 percent (according to HPLC), corresponding to a yield of 83.3 percent, relative to the cyclobutanedione, was obtained. Data for the title compound was:

Melting point: 88° C.-90° C.

$^1$H-NMR: (CDCl$_3$, 300 MHz) δin ppm 1.10-1.49, m, 5H.

1.65-1.80, bd, 1H.

1.88-2.01, bd, 2H.

2.04-2.13, bd, 2H.

2.78-2.91, m, 1H.

2.66, b, 6H.

13.2, b, 1H.

(b) 3.24 g of 3-acetoxy-2-cyclobuten-1-one (triketene, 25.0 mmol) was dissolved in 1.90 g of absolute ethanol (41.3 mmol) and 40 g of ethyl acetate. 6.45 g of cyclohexyldimethylamine (99 percent; 50.0 mmol), dissolved in 10 g of ethyl acetate, was instilled in this solution at 20° C. within 20 minutes. After 2 hours of stirring at room temperature, the suspension was filtered and dried under vacuum. 4.09 g of the title product with a content of 94.5 percent (according to HPLC), corresponding to a yield of 73.2 percent, relative to the 3-acetoxy-2-cyclobuten-1-one (triketene), was obtained. Data for the title compound was:

Melting point: 91.5° C.-92.4° C.

EXAMPLE 4

Production of 3-hydroxy-2-cyclobuten-1-one-dicyclohexylmethyl ammonium salt (a) A solution of 4.99 g of dicyclohexylmethylamine (25.0 mmol) in 10 g of ethyl acetate was instilled in a suspension of 2.11 g of 1,3-cyclobutanedione (23.0 mmol) at 20° C. and stirred for 1 hour. After another 30 minutes of stirring at 5° C., the suspension was filtered and dried under vacuum. 5.53 g of the title product with a purity of 94.7 percent (according to HPLC), corresponding to a yield of 81.4 percent, relative to the cyclobutanedione, was obtained. Data for the title compound was:

Melting point: 91.4° C.-92.6° C.

(b) 3.24 g of 3-acetoxy-2-cyclobuten-1-one (triketene, 97.5 percent; 25.0 mmol) was dissolved in 1.9 g of ethanol (41.3 mmol) and 40 g of ethyl acetate. 9.83 g of dicyclohexylmethylamine (98.9 percent; 50.0 mmol), dissolved in 10 g of ethyl acetate, was instilled in this solution at 20° C. in 15 minutes and stirred for 1 hour at room temperature. After another hour of stirring at 5° C., the suspension was filtered and dried under vacuum. 3.21 g of the title product with a content of 94.5 percent (according to HPLC), corresponding to a yield of 43.5 percent, relative to the 3-acetoxy-2-cyclobuten-1-one, was obtained. Data for the title compound was:

Melting point: 91.4° C.-92.4° C.

$^1$H-NMR: (CDCl$_3$, 300 MHz) δin ppm 1.09-1.42, m, 6H 1.42-1.66, bd, 4H.

1.67-1.78, bd, 2H.

1.88-2.03, bd, 4H.

2.04-2.16, bd, 4H.

2.64, s, 3H.

2.93, b, 2H.

3.13, m, 2H.

4.33, b, 1H.

EXAMPLE 5

Production of 3-hydroxy-2-cyclobuten-1-one dicyclohexylammonium salt (a) A solution of 7.1 g of dicyclohexylamine (98 percent; 38.3 mmol) in 15 ml of ethyl acetate was instilled in a suspension of 3.0 g of 1,3-cyclobutanedione (97 percent; 34.6 mmol) in ethyl acetate (52.2 ml) at 20° C. in 15 minutes. After 1 hour of stirring at room temperature, the suspension was washed four times with ethyl acetate and dried under vacuum. 9.4 g of the title product with a content of 94.7 percent (according to HPLC), corresponding to a yield of 96.7 percent, relative to cyclobutanedione, was obtained. Data for the title compound was:

Melting point: 188° C.-188.7° C.

(b) 1000 g of distillation residue from diketene production, containing 22.0 percent of 3-acetoxy-2-cyclobuten-1-one (1.74 mol), was dissolved in 1078 ml of (970 g). 707.4 g of dicyclohexylamine (98 percent; 3.81 mol) was instilled in this black solution at 10° C. within 60 minutes. After 90 minutes, of stirring at +10° C., the suspension was filtered, suspended three times with ethyl acetate and dried under vacuum. 518 g of the title product with a content of 65.5 percent (HPLC), corresponding to a yield of 73.4 percent, relative to 3-acetoxy-2-cyclobuten-1-one, was obtained. Data for the title compound was:

Melting point: 169.7° C.-172.4° C.

Purification of the title compound: 259 g of 3-hydroxy-2-cyclobuten-1-one dicyclohexylammonium salt (crude; 65.5 percent; 0.64 mol) was suspended in 207.2 g of glacial acetic acid and 310.8 g of ethyl acetate, and stirred for 2 hours at room temperature. The product was washed three times with ethyl acetate and dried under vacuum. 176 g of the title product with a content of 90.2 percent (according to HPLC) corresponding to a yield of 93.6 percent was obtained. Data for the purified title compound was:

Melting point: 188° C.-190° C.

1.66-1.80, bd 2H.

1.80–1.97, bd, 4H.
2.81, s, 2H.
4.29, s, 1H.
3.09–3,27, m, 2H.

EXAMPLE 6

Production of 3-hydroxy-2-cyclobuten-1-one ammonium salt (a) A solution of 0.425 g of ammonia gas (25 mol) in 25 g of acetonitrile as instilled in a solution of 2.16 g of 1,3-cyclobutanedione (97 percent; 25.0 mmol) in 25 g of acetonitrile at 20° C. within 10 minutes. After 30 minutes of stirring at room temperature, the suspension was filtered, washed with acetonitrile (10 ml) and dried under vacuum. 1.48 g of the title product with a content of 78 percent (according to HPLC), corresponding to a yield of 47.0 percent, relative to the cyclobutanedione, was obtained. Data for the title compound was:
Melting point: 94° C.–96° C.

(b) 3.1 g of ammonia gas (182.3 mmol) was introduced in a solution of 6.5 g of 3-acetoxy-2-cyclobuten-1-one (triketene, 97 percent; 50.0 mmol) in 58.5 g of acetonitrile at 2° C. within 30 minutes. The reaction mixture was stirred for another 30 minutes at 2° C., then filtered, washed with acetonitrile (20 ml) and dried under vacuum. 4.88 g of the title product with a content (according to HPLC) of 94 percent, corresponding to a yield of 90.7 percent, relative to the 3-acetoxy-2-cyclobuten-1-one, was obtained. Data for the title compound was:
Melting point: 109° C.–110° C.
$^1$H-NMR: (d$_6$-DMSO) $\delta$ in ppm, 2.49, s, 2H.
3.91, s, 1H.
7.25, b, 4H.

EXAMPLE 7

Production of 3-hydroxy-2-cyclobuten-1-one sodium salt (a) A solution of sodium ethanolate containing 0.506 g of sodium (22 mmol) in 15 g of absolute ethanol was instilled in a solution of 1.74 g of 1,3-cyclobutanedione (97 percent; 20.0 mmol) in 20 g of acetonitrile at 20° C. in 20 minutes. After 15 minutes, the reaction mixture was stirred at room temperature, then filtered and dried under vacuum. 1.58 g of the title product with a purity of 92.6 percent (according to HPLC), corresponding to a yield of 69.0 percent, relative to the cyclobutanedione, was obtained. Data for the title compound was:
Melting point: greater than 280° C.
$^1$H-NMR: (d$_6$-DMSO) $\delta$ in ppm. 2.49, s, 2H.
3.92, s, 1H.

(b) A solution of 1.099 g of sodium hydroxide (27 mmol) in absolute ethanol (10 g) was instilled in a solution of 3.23 g of 3-acetoxy-2-cyclobuten-1-one (triketene, 97.5 percent; 25.0 mmol) in 20 g of acetonitrile at 20° C. within 15 minutes. After about 2 hours of stirring, the suspension was filtered at room temperature, washed with acetonitrile (5 ml) and dried under vacuum. 2.38 g of the title product with a content of 87.2 percent (according to HPLC), corresponding to a yield of 89.8 percent, relative to the 3-aceoxy-2-cyclobuten-1-one, was obtained.

(c) A solution of 4.6 g of sodium hydroxide (115 mmol) in 75 g of absolute ethanol was instilled in a solution of 28.4 g of distillation residue from the diketene production with a content of 44.4 percent of 3-acetoxy-2-cyclobuten-1-one (triketene; 98 mmol) in 250 g of ethyl acetate in 45 minutes at 10° C. The suspension was filtered. The residue was dried under vacuum. 17.1 g of the title product with a content of 46.7 percent (according to HPLC) corresponding to a yield of 75.3 percent, relative to the 3-acetoxy-2-cyclobuten-1-one, was obtained.

EXAMPLE 8

Production of 3-hydroxy-2-cyclobuten-1-one potassium salt

A solution of 1.8 g of potassium hydroxide (27.5 mmol) in absolute ethanol (40 g) was instilled in a solution of 3.23 g of 3-acetoxy-2-cyclobuten-1-one (triketene, 97.5 percent; 25 mmol) in acetonitrile (20 g) at room temperature within 10 minutes. After 30 minutes of stirring, the suspension was filtered at room temperature, washed with acetonitrile (5 ml) and dried under vacuum. 1.99 g of the title product with a content of 81.5 percent (according to HPLC), corresponding to a yield of 53.1 percent, relative to the 3-acetoxy-2-cyclobuten-1-one, was obtained. Data for the title compound was:
Melting point: greater than 260° C.

EXAMPLE 9

Production of Squaric Acid (a) 3.66 g (50 mmol) of 3-hydroxy-2-cyclobuten-1-one dicyclohexylammonium salt was suspended in methylene chloride (100 ml) and cooled to −20° C. Then, 10.63 g (150 mmol) of chlorine gas was introduced. After a reaction time of 30 minutes, it was heated with stirring to room temperature, methylene chloride was distilled off in a Rotavapor, and ethyl acetate (100 ml) was added. The precipitate was filtered and the mother liquor was concentrated by evaporation in a Rotavapor. The residue thus obtained (11.63 g) was stirred with concentrated sulfuric acid (25 ml) of 15 hours at 100° C. After cooling with an ice bath, the precipitate was filtered, then washed three times with acetone (20 ml) and dried for 15 hours at 50° C. and 50 mbars. 1.22 g of gray powder with a content of 88 percent of squaric acid, corresponding to a yield of 19 percent, relative to the 3-hydroxy-2-cyclobuten-1-one cyclohexylammonium salt, was obtained.

(b) 73.2 g (1 mol) of 3-hydroxy-2-cyclobuten-1-one dicyclohexylammonium salt was suspended in ethyl acetate (1.5 l) and then cooled to 0° C. 474.5 g of bromine (3 mol) in ethyl acetate (500 ml) was added with stirring. The precipitate was filtered after 30 minutes and washed twice with ethyl acetate (250 ml). The mother liquor and washing solutions were combined and concentrated by evaporation. 442.75 g of residue remained. Then, 415.25 g of this residue was added to water (34 g) and sulfuric acid (500 ml). After 12 hours of stirring at room temperature, the precipitate was filtered and washed twice with acetone (100 ml). 111.47 g of white title product with a squaric acid content of 94.6 percent, corresponding to a yield of 92.45 percent, relative to the 3-hydroxy-2-cyclobuten-1-one dicyclohexylammonium salt used, was obtained.

(c) 3.66 g (50 mmol) of 3-hydroxy-2-cyclobuten-1-one dicyclohexylammonium salt was suspended in ethyl acetate (100 ml). Then 20.25 g of sulfuryl chloride (150 mmol) was instilled at room temperature with stirring. After a reaction time of 1 hour, it was suspended with ethyl acetate (50 ml), then filtered, and the filtrate was concentrated by evaporation in a Rotavapor. 11.7 g of a semiliquid residue remained. 11.7 g of this material was added to concentrated sulfuric acid (25 ml) and water (1.7 g). After a reaction time of 2 hours, the residue was filtered and washed four times with acetone (5 ml). 1.3 g of the title product with a squaric acid content of 9.29 percent, corresponding to a yield of 23.14 percent relative to the 3-hydroxy-2-cyclobuten-1-one dicyclohexylammonium salt used, was obtained.

(d) 3.66 g (50 mmol) of 3-hydroxy-2-cyclobuten-1-one dicyclohexylammonium salt was suspended in ethyl acetate (100 ml). After the addition of 3.95 g of bromine (25 mmol) within 20 minutes, 16.87 g of sulfuryl chloride (125 mmol) was instilled in 30 minutes with stirring. After a reaction time of a total of 105 minutes, the precipitate was washed twice with ethyl acetate (50 ml) and the mother liquor and washing solutions were combined and concentrated by evaporation. The residue (11.32 g) was added to concentrated sulfuric acid (25 ml) and water (1.7 g) at 100° C. After a reaction time of 2 hours, the residue was filtered and washed four times with acetone (5 ml). 5.26 g of white title product with a squaric acid content of 92.7 percent, corresponding to a yield of 85.4 percent, relative to the 3-hydroxy-2-cyclobuten-1-one dicyclohexylammonium salt used, was obtained.

EXAMPLE 10

Production of 1,3-cyclobutanedione starting from 1,3-cyclobutanedione dicyclohexylammonium salt 146.0 g (0.5 mol) of 1,3-cyclobutanedione dicyclohexylammonium salt with a content of 90.9 percent (according to HPLC) was suspended in acetonitrile (1,400 ml) and cooled to 10° C. 21.0 g of HCl gas (0.573 mol) was introduced in this light brown suspension within 20 minutes. The reaction mixture as then stirred for another 30 minutes at 10° C. and then filtered. Then the aminohydrochloride was washed with acetonitrile (100 ml). Then it was concentrated in a vacuum up to 220 g, cooled for 30 minutes in an ice bath, filtered, washed twice with ether (100 ml) and dried at room temperature for 10 minutes at 20 mbars. 32.07 of the title product with a content of 89.8 percent (according to HPLC), corresponding to a yield of 68.5 percent, relative to the cyclobutanedione dicyclohexylamine salt, was isolated. Data for the title compound was:

Melting point: 103°–105° C. (decomposition).
$^1$H-NMR: ($d_6$-DMSO) δ in ppm 3.06, s, 2H.
4.75, s, 1H.
9.5–12.5, b, 1H.

What is claimed is:

1. A 3-hydroxy-2cyclobuten-1-one salt of the formula:

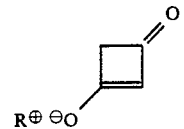

wherein R is an ammonium group of the formula:

wherein which $R_1$, $R_2$ and $R_3$ are the same or different in meaning and each is a hydrogen atom, a lower alkyl group or a cycloalkyl group, or R is an alkali metal atom.

2. The salt as claimed in claim 1 wherein, in the ammonium group, $R_1$, $R_2$ and $R_3$ are the same or different in meaning and each is a hydrogen atom, a $C_1$–$C_4$ lower alkyl group or a cyclohexyl group.

3. The salt as claimed in claim 1 which is 3-hydroxy-2-cyclobuten-1-one diethylammonium salt.

4. The salt as claimed in claim 1 which is 3-hydroxy-2-cyclobuten-1-one cyclohexyldimethylammonium salt.

5. The salt as claimed in claim 1 which is 3-hydroxy-2-cyclobuten-1one cyclohexyldimethylammonium salt.

6. The salt as claimed in claim 1 which is 3-hydroxy-2-cyclobuten-1-one dicyclohexylammonium salt.

7. The salt as claimed in claim 1 which is 3-hydroxy-2-cyclobuten-1-one dicyclohexylmethylammonium salt.

8. The salt as claimed in claim 1 which is 3-hydroxy-2-cyclobuten-1-one ammonium salt.

9. The salt as claimed in claim 1 which is 3-hydroxy-2-cyclobuten-1-one sodium salt.

10. The salt as claimed in claim 1 which is 3-hydroxy-2-cyclobuten-1one potassium salt.

* * * * *